United States Patent
Dimalanta

(10) Patent No.: US 8,308,735 B2
(45) Date of Patent: Nov. 13, 2012

(54) PHACOEMULSIFICATION TIP WITH INTERNAL ORIENTED STRUCTURES

(75) Inventor: Ramon C. Dimalanta, Trabuco Canyon, CA (US)

(73) Assignee: Novartis AG, Basel (CH)

( * ) Notice: Subject to any disclaimer, the term of this patent is extended or adjusted under 35 U.S.C. 154(b) by 553 days.

(21) Appl. No.: 12/245,872

(22) Filed: Oct. 6, 2008

(65) Prior Publication Data

US 2010/0087846 A1    Apr. 8, 2010

(51) Int. Cl.
*A61F 9/00* (2006.01)
(52) U.S. Cl. .......................... 606/107; 604/22
(58) Field of Classification Search .............. 606/4, 107, 606/169, 170; 604/22, 275; 600/437; 623/6.11, 623/6.12
See application file for complete search history.

(56) References Cited

U.S. PATENT DOCUMENTS

| | | | |
|---|---|---|---|
| 3,589,363 A | 6/1971 | Banko | |
| 4,223,676 A | 9/1980 | Wuchinich | |
| 4,246,902 A | 1/1981 | Martinez | |
| 4,493,694 A | 1/1985 | Wuchinich | |
| 4,515,583 A | 5/1985 | Sorich | |
| 4,589,415 A | 5/1986 | Haaga | |
| 4,609,368 A | 9/1986 | Dotson, Jr. | |
| 4,816,018 A | 3/1989 | Parisi | |
| 4,869,715 A | 9/1989 | Sherburne | |
| 4,922,902 A | 5/1990 | Wuchinich et al. | |
| 4,989,583 A | 2/1991 | Hood | |
| 5,151,099 A * | 9/1992 | Young et al. | 606/27 |
| 5,154,694 A | 10/1992 | Kelman | |
| 5,359,996 A | 11/1994 | Hood | |
| 5,725,495 A * | 3/1998 | Strukel et al. | 604/44 |
| 5,984,904 A | 11/1999 | Steen et al. | |
| 5,989,209 A * | 11/1999 | Barrett | 604/22 |
| 6,007,555 A | 12/1999 | Devine | |
| 6,159,175 A | 12/2000 | Strukel et al. | |
| 6,283,974 B1 | 9/2001 | Alexander | |
| 6,354,331 B1 | 3/2002 | Fisher et al. | |
| 6,533,750 B2 | 3/2003 | Sutton et al. | |
| 6,605,078 B2 * | 8/2003 | Adams | 606/1 |
| 2002/0151917 A1 * | 10/2002 | Barry | 606/159 |
| 2006/0217739 A1 | 9/2006 | Tjia et al. | |
| 2007/0060926 A1 * | 3/2007 | Escaf | 606/107 |

OTHER PUBLICATIONS

International Search Report for PCT/US2006/008069, Publication No. WO2006/101717, 2 pages.

* cited by examiner

*Primary Examiner* — Victor Nguyen
(74) *Attorney, Agent, or Firm* — Darien Reddick

(57) ABSTRACT

A phacoemulsification tip is formed from a tube that encloses an aspiration lumen surrounded by and generally concentric with a structure section. The structure section has a plurality of structures (ridges, vanes, ribs, or fins). The plurality of structures project inward from an inner wall of the tube at the distal end of the tube. The plurality of the structures are disposed at an angle with respect to a face of the distal end of the tube. Alternatively, the plurality of the structures are disposed at a non-perpendicular angle with respect to a plane that is tangent to a curved outer surface of the tube.

10 Claims, 3 Drawing Sheets

PHACOEMULSIFICATION TIP WITH INTERNAL ORIENTED STRUCTURES

BACKGROUND OF THE INVENTION

This invention relates generally to the field of phacoemulsification and more particularly to phacoemulsification cutting tips.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an IOL.

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

In use, the ends of the cutting tip and irrigating sleeve are inserted into a small incision of predetermined width in the cornea or sclera. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

In one phacoemulsification procedure the horn is driven to produce oscillatory or rotational movement at the tip. Driving the tip in a torsional motion produces more effective cutting and less repulsion of lens material. Torsional tip motion also lends itself to improved tip designs. One such design is described herein.

SUMMARY OF THE INVENTION

In one embodiment of the present invention, a phacoemulsification tip comprises a tube having a generally circular cross section and a distal end. The distal end has an opening. The tube encloses an aspiration lumen surrounded by and generally concentric with a structure section. The structure section comprises a plurality of structures selected from the group consisting of ridges, vanes, ribs, and fins. The plurality of structures project inward from an inner wall of the tube at the distal end of the tube. The plurality of the structures are oriented at an angle with respect to a face of the distal end of the tube.

In another embodiment of the present invention, a phacoemulsification tip comprises a tube having a generally circular cross section and a distal end. The distal end has an opening. The tube encloses an aspiration lumen surrounded by and generally concentric with a structure section. The structure section comprises a plurality of structures selected from the group consisting of ridges, vanes, ribs, and fins. The plurality of structures project inward from an inner wall of the tube at the distal end of the tube. The plurality of the structures are disposed at a non-perpendicular angle with respect to a plane that is tangent to a curved outer surface of the tube.

DETAILED DESCRIPTION OF THE INVENTION

Reference is now made in detail to the exemplary embodiments of the invention, examples of which are illustrated in the accompanying drawings. Wherever possible, the same reference numbers are used throughout the drawings to refer to the same or like parts.

Figure 1:
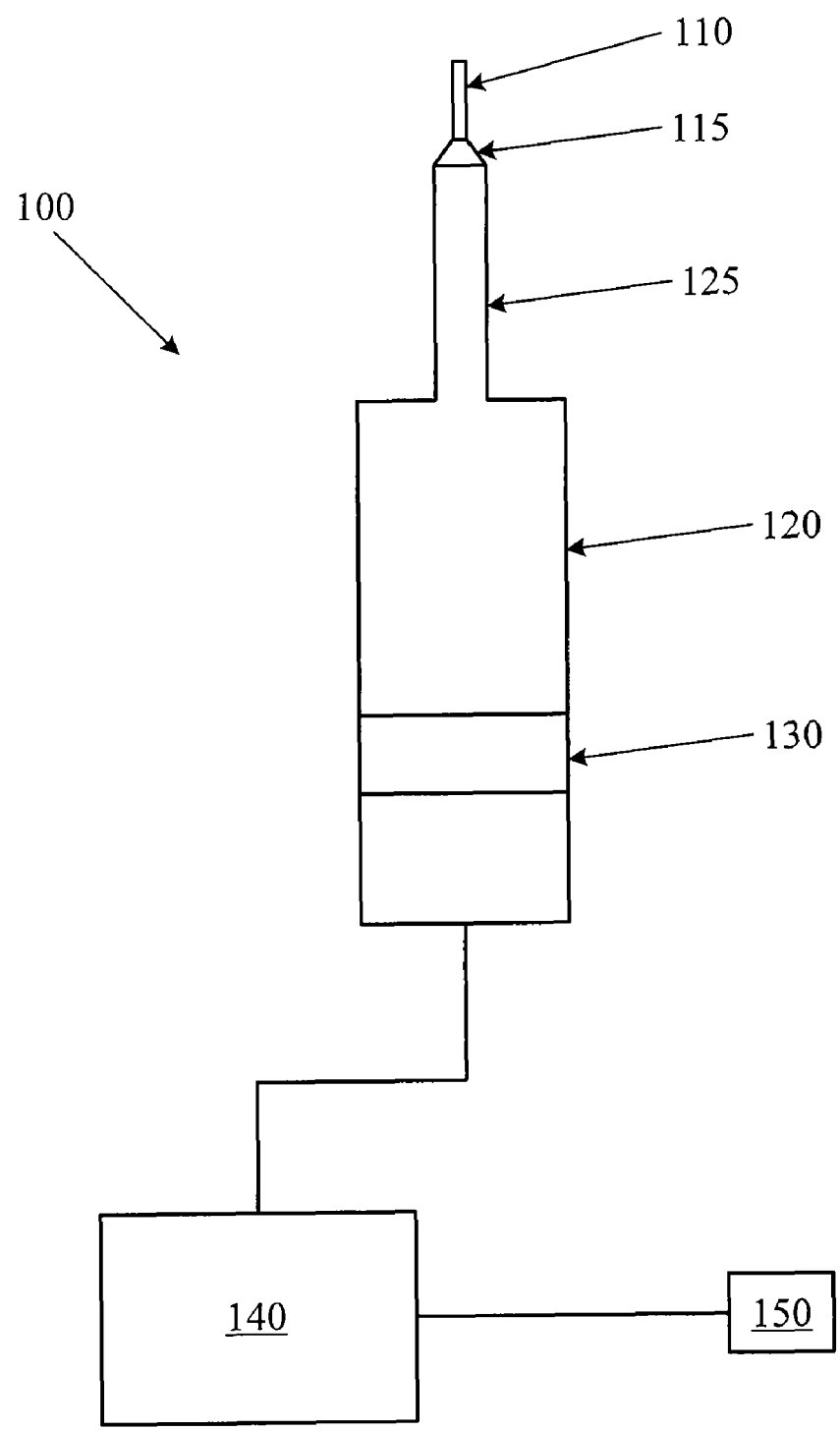
FIG. 1 depicts the operative portion of an ultrasonic hand piece.

FIG. 1 depicts an ultrasonic hand piece. In FIG. 1, hand piece 100 is coupled to console 140. Console 140 is coupled to foot switch 150. Hand piece 100 has a cutting tip 110, a horn 120, and a set of piezoelectric crystals 130. A tip interface 115 connects cutting tip 110 to a reduced diameter portion 125 of horn 120.

Tip 110 is typically a thin needle made of titanium or stainless steel that is designed to emulsify a lens when vibrated ultrasonically. Tip 110 is typically cylindrical in shape, has a small diameter of about 20-30 gauge, and has a length suitable for removal of a lens when inserted into the anterior chamber of the eye.

Horn 120 is typically made of a rigid material suitable for medical use (such as a titanium alloy). Horn 120 has a reduced diameter section 125 that is connected to a tip interface 115. Tip interface 115 typically has a threaded connection that accepts tip 110. In this manner tip 110 is screwed onto horn 120 at tip interface 115. This provides a rigid connection between tip 110 and horn 120 so that vibration can be transmitted from horn 120 to tip 110.

Piezoelectric crystals 130 supply ultrasonic vibrations that drive both the horn 120 and the attached cutting tip 110 during phacoemulsification. Piezoelectric crystals 130 are affixed to horn 120. Crystals 130 are typically ring shaped, resembling a hollow cylinder and constructed from a plurality of crystal segments. When excited by a signal from console 140, crystals 130 resonate, producing vibration in horn 120.

Console 140 includes a signal generator that produces a signal to drive piezoelectric crystals 130. Console 140 has a suitable microprocessor, micro-controller, computer, or digital logic controller to control the signal generator. In operation, console 140 produces a signal that drives piezoelectric crystals 130. Piezoelectric crystals 130, when excited, cause horn 120 to vibrate. Tip 110, connected to horn 120, also vibrates. When tip 110 is inserted into the anterior chamber of the eye and vibrated, it acts to emulsify a cataractous lens.

Figure 2:
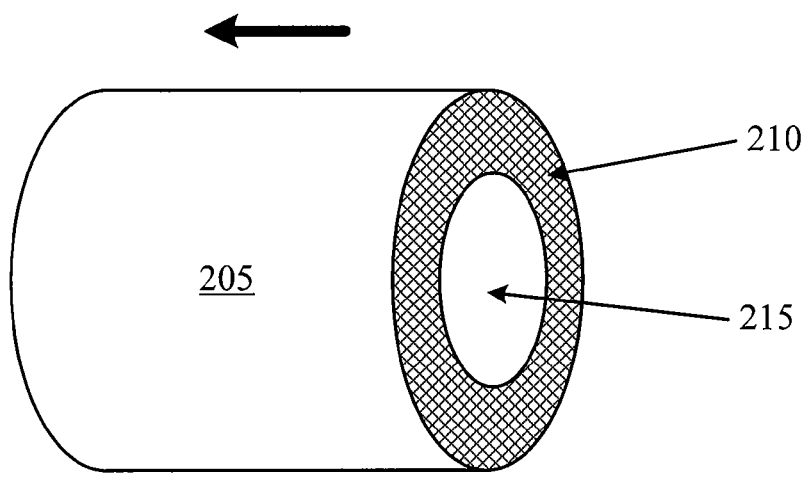
FIG. 2 is a perspective view of the end of a cutting tip according to the principles of the present invention.

FIG. 2 is a perspective view of the end of a cutting tip according to the principles of the present invention. The end of cutting tip 205 is generally cylindrical with a section 210 that contains ridges, ribs, vanes, fins, or the like (hereinafter referred to as "structure" or "structures") and a section 215 that forms an aspiration lumen. In this manner, a central aspiration lumen section 215 is surrounded by and concentric with a section 210 that contains the structures. Lens material is cut by tip 205 when it is ultrasonically vibrated and aspirated through aspiration lumen section 215. The presence of structures in section 210 assists to improve cutting and/or improve the removal of lens material as better described below. A front face of tip 205 lies in a plane that is coplanar with the shaded region (210) of FIG. 2. The bold arrow shows the direction of aspiration or removal of lens material through the tip.

Figure 3:
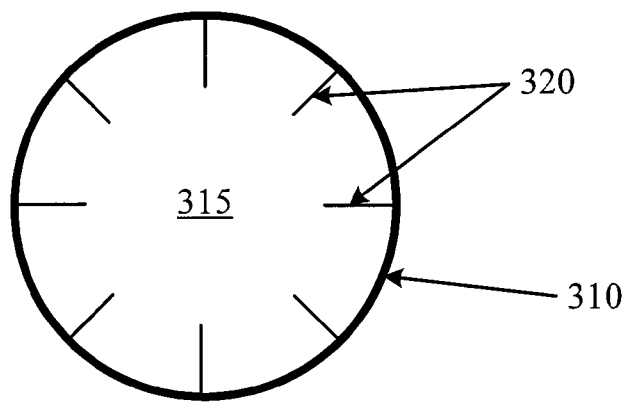
FIG. 3 is an end view of a cutting tip according to the principles of the present invention.

FIG. 3 is an end view of a cutting tip according to the principles of the present invention. In this view, aspiration lumen 315 is surrounded by structures 320 that protrude from the interior surface of cutting tip 310. Cutting tip 310, as previously noted, is generally cylindrical in shape and has a generally circular cross section as depicted in FIG. 3. The wall of cutting tip 310 has thickness that yields a suitably rigid tube to which the structures 320 are attached. In the embodiment of FIG. 3, the structures 320 are generally perpendicular to a tangent line drawn on the circular cross section of cutting tip 310. They are also evenly spaced. In other embodiments, the structure 320 need not be evenly spaced.

Figure 4:
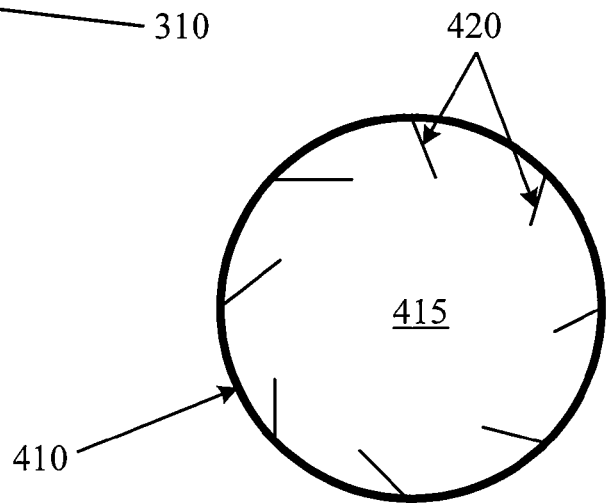
FIG. 4 is an end view of a cutting tip according to the principles of the present invention.

FIG. 4 is an end view of a cutting tip according to the principles of the present invention. In this view, aspiration lumen 415 is surrounded by structures 420 that protrude from the interior surface of cutting tip 410. Cutting tip 410, as previously noted, is generally cylindrical in shape and has a generally circular cross section as depicted in FIG. 4. The wall of cutting tip 410 has thickness that yields a suitably rigid tube to which the structures 420 are attached. In the embodiment of FIG. 4, the structures 420 are not perpendicular to a tangent line drawn on the circular cross section of cutting tip 410. In this manner, the angle of the structure 420 can vary with respect to a tangent line drawn on the circular cross section of cutting tip 410. This angle can be adjusted to optimize the cutting properties of tip 410. In addition, this angle can be adjusted to optimize the manner in which aspirated material is removed from through aspiration lumen 415. For example, when the structures 420 are oriented as shown in FIG. 4, rotation of tip in one direction causes structures 420 to bite into lens material, more effectively cutting it. When rotated in the opposite direction, cutting action is lessened and aspiration may be improved.

Figure 5:
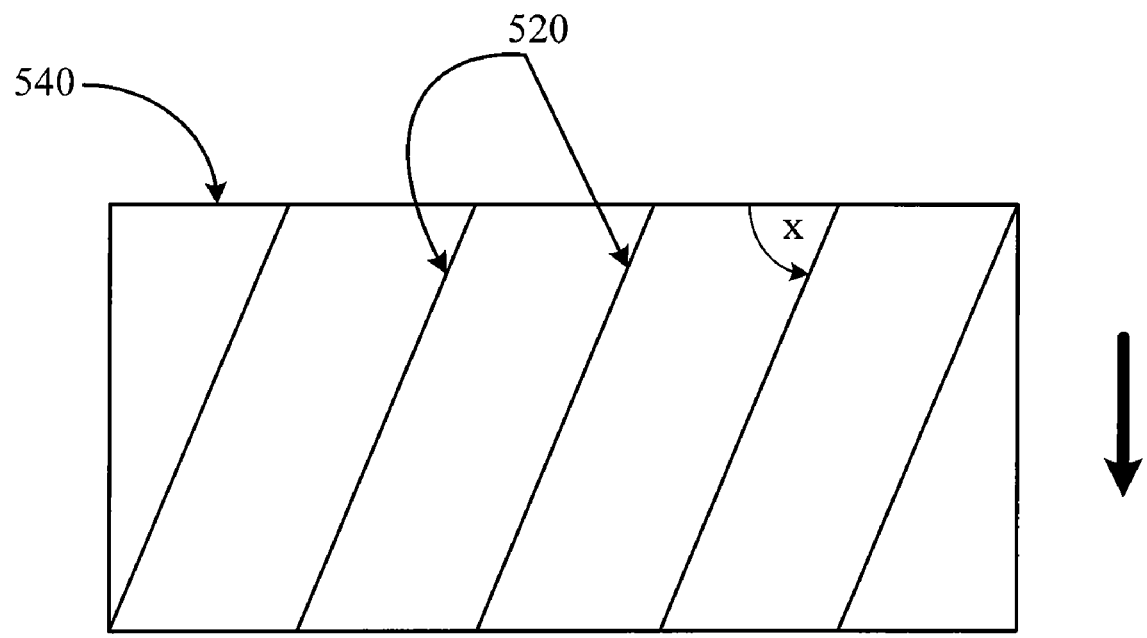
FIG. 5 is an unrolled view of a cutting tip according to the principles of the present invention.

FIG. 5 is an unrolled view of a cutting tip according to the principles of the present invention. In this view, the generally cylindrical tip is unrolled to expose the orientation of the structures 520. Generally, the structures 520 are oriented at an angle with respect to a face 540 of the distal end of the tip. The face 540 of the tip is located at the distal end of the tip. The structures 520 are oriented at an angle of x degrees with respect to the face 540 of the cutting tip. This angle is preferably between about five and 85 degrees. In this embodiment, the structures 520 are generally linear. When rotated in one direction, the structures 540 act to enhance cutting as the angle x causes the structures to bite into the lens material. When rotated in the opposite direction, the structures 540 act to reduce cutting action as the angle x causes the structures to assist in aspiration of the lens material. Additionally, the structures 520 may be generally perpendicular to the inner wall of the tip as shown in FIG. 3, or they may be oriented at an angle as shown in FIG. 4 (resulting in structures 520 being oriented at a compound angle with respect to the inner wall of the tip). The bold arrow shows the direction of aspiration or removal of lens material through the tip.

Figure 6:
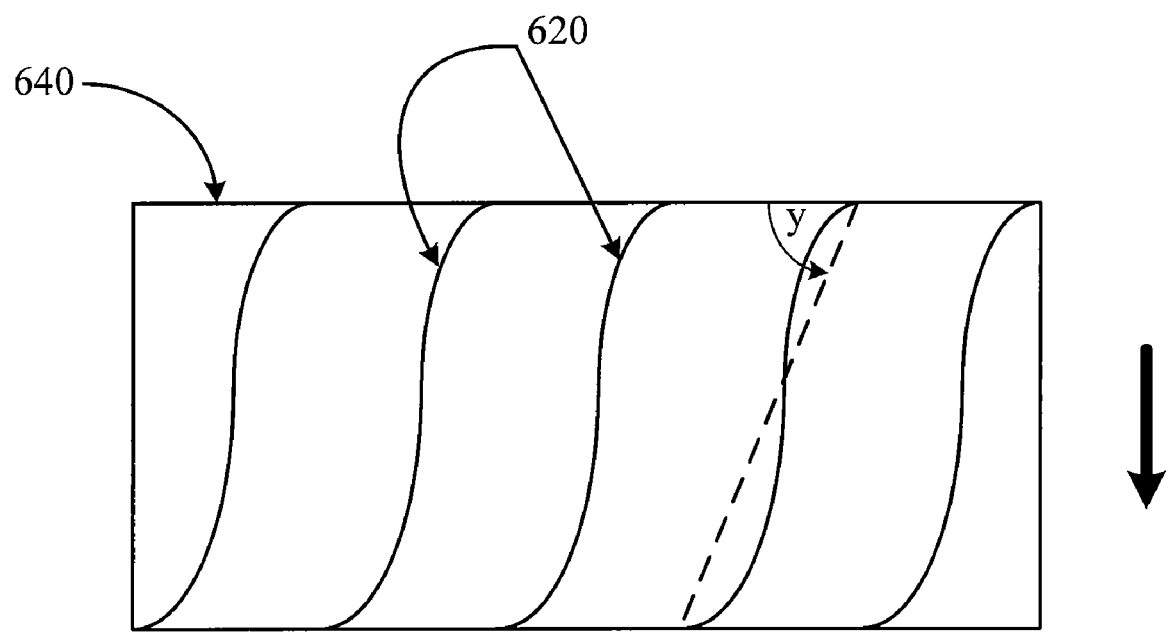
FIG. 6 is an unrolled view of a cutting tip according to the principles of the present invention.

FIG. 6 is an unrolled view of a cutting tip according to the principles of the present invention. In this view, the generally cylindrical tip is unrolled to expose the orientation of the structure 620. Generally, the structures 620 are oriented at an angle with respect to the face 640 of the distal end of the tip. The structures 620 are oriented at an angle of y degrees with respect to the face 640 of the cutting tip. This angle is preferably between about five and 85 degrees. In this embodiment, the structures 620 are not linear—instead having a curved or spiral shape. Additionally, the structures 620 may be generally perpendicular to the inner wall of the tip as shown in FIG. 3, or they may be oriented at an angle as shown in FIG. 4 (resulting in structures 620 being oriented at a compound angle with respect to the inner wall of the tip). The bold arrow shows the direction of aspiration or removal of lens material through the tip.

When the tips of FIGS. 2-6 are coupled to a phacoemulsification hand piece that produces torsional or oscillatory movement at the tip, the structures are oriented such that they enhance the cutting action when rotated in one direction and enhance the removal of lens material (or assist aspiration) when rotated in the other direction. In this manner, the structures can act much like the cutting surfaces of a drill bit. The structures are also more effective at reducing occlusions—i.e. a blockage of the aspiration lumen that results in an increase in aspiration pressure. Further, the faces or edges of the structures may be sharpened or serrated to promote cutting of the lens material. They may also be rounded or blunt to promote removal of lens material. In another example, the front face or edge may be sharpened to promote cutting when the tip is rotated in one direction, and the back face or edge may be blunt or rounded to promote removal when the tip is rotated in the opposite direction.

From the above, it may be appreciated that the present invention provides an improved phacoemulsification tip useful for the removal of a cataractous lens. In the present invention, the cutting tip is has a plurality of internal oriented structures. These structures facilitate cutting and/or removal of lens material. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A phacoemulsification tip comprising:
    a tube having a generally circular cross section and a distal end, the distal end having an opening, the tube enclosing an aspiration lumen surrounded by and generally concentric with a structure section, the aspiration lumen extending through an entire length of the tube;
    wherein the structure section comprises a plurality of structures selected from the group consisting of ridges, vanes, ribs, and fins, the plurality of structures projecting inward from an inner wall of the tube at the distal end of the tube, the plurality of the structures oriented at an angle with respect to a face of the distal end of the tube;
    wherein further comprising a coupling configured to couple to a tip interface of an ultrasonic hand piece; and
    wherein the tube is formed from a rigid material.

2. The phacoemulsification tip of claim 1 wherein the angle is between about five and 85 degrees.

3. The phacoemulsification tip of claim 1 wherein the plurality of structures are generally linear.

4. The phacoemulsification tip of claim 1 wherein the plurality of structures are curved.

5. The phacoemulsification tip of claim 1 wherein the plurality of structures have a spiral shape.

6. The phacoemulsification tip of claim 1 wherein the plurality of structures are generally perpendicular to a plane that is tangent to the outer surface of the tube.

7. The phacoemulsification tip of claim 1 wherein the plurality of structures are disposed at a non-perpendicular angle with respect to a plane that is tangent to a curved outer surface of the tube.

8. The phacoemulsification tip of claim 1, wherein ends of the plurality of structures are freely extending.

9. The phacoemulsification tip of claim 1, wherein the plurality of structures extend to a distal end face of the tube.

10. The phacoemulsification tip of claim 1, wherein the rigid material comprises titanium or stainless steel.

* * * * *